United States Patent
Wintermute et al.

(10) Patent No.: US 11,534,328 B2
(45) Date of Patent: Dec. 27, 2022

(54) COLOSTOMY CLIP BAG HOLDER

(71) Applicants: Dean E. Wintermute, Cooper, TX (US); Delinda Leatherwood, Cooper, TX (US)

(72) Inventors: Dean E. Wintermute, Cooper, TX (US); Delinda Leatherwood, Cooper, TX (US)

( * ) Notice: Subject to any disclaimer, the term of this patent is extended or adjusted under 35 U.S.C. 154(b) by 925 days.

(21) Appl. No.: 16/258,775

(22) Filed: Jan. 28, 2019

(65) Prior Publication Data
US 2019/0274870 A1    Sep. 12, 2019

Related U.S. Application Data

(60) Provisional application No. 62/641,353, filed on Mar. 11, 2018.

(51) Int. Cl.
| | | |
|---|---|---|
| *A61F 5/449* | (2006.01) | |
| *A61F 5/448* | (2006.01) | |
| *A61F 5/44* | (2006.01) | |

(52) U.S. Cl.
CPC ............ *A61F 5/449* (2013.01); *A61F 5/4407* (2013.01); *A61F 5/448* (2013.01); *A61F 2005/4486* (2013.01)

(58) Field of Classification Search
CPC ........ A61F 5/449; A61F 5/4407; A61F 5/448; A61F 2005/4486
See application file for complete search history.

(56) References Cited

U.S. PATENT DOCUMENTS

| | | | | |
|---|---|---|---|---|
| 3,865,109 | A * | 2/1975 | Elmore ................... | A61F 5/441 604/339 |
| 4,427,110 | A * | 1/1984 | Shaw, Jr. ............... | A61B 50/37 220/495.11 |
| 5,022,553 | A * | 6/1991 | Pontius .................... | B65F 7/00 229/125.37 |
| 5,154,499 | A * | 10/1992 | Atkinson ............ | A61M 5/1415 403/91 |
| 5,343,634 | A * | 9/1994 | Dailey .................... | A61F 5/445 34/104 |
| 5,423,782 | A * | 6/1995 | Wolrich .................. | A61F 5/445 604/339 |
| 5,591,144 | A * | 1/1997 | Smith ..................... | A61F 5/445 604/327 |
| 5,865,819 | A * | 2/1999 | Cisko, Jr. ................ | A61F 5/445 604/338 |
| 5,938,647 | A * | 8/1999 | Smith ..................... | A61F 5/445 604/332 |
| 6,457,863 | B1 * | 10/2002 | Vassallo ................. | B65D 75/30 150/900 |

(Continued)

*Primary Examiner* — Guy K Townsend
(74) *Attorney, Agent, or Firm* — Wilson D Swayze, Jr.

(57) ABSTRACT

A closure assistant for colostomy bag clip is disclosed. The closure assistant helps a patient in closing and opening of the colostomy bag clip. The closure assistant consists of a flat panel with multiple slots on its upper surface. The slots are designed to fit different types of clips of the colostomy bag. The slots of the closure assistant are of different shapes to support different kinds of clips. The closure assistant accommodates either curved or linear type of clips. The closure assistant helps the patients, suffering from medical issues requiring an ostomy pouching system or colostomy bag and the related problems of using colostomy bag.

15 Claims, 5 Drawing Sheets

(56) References Cited

U.S. PATENT DOCUMENTS

| | | | |
|---|---|---|---|
| 10,307,286 B2* | 6/2019 | Hosono | A61F 5/445 |
| 10,449,429 B2* | 10/2019 | Bruce | A63B 55/40 |
| 2002/0162304 A1* | 11/2002 | Stravitz | B65F 1/12 |
| | | | 53/526 |
| 2004/0069661 A1* | 4/2004 | Telleen | G06Q 30/0273 |
| | | | 206/37.1 |
| 2005/0159717 A1* | 7/2005 | Holtermann | A61F 5/4407 |
| | | | 604/332 |
| 2007/0027434 A1* | 2/2007 | Pedersen | A61F 5/441 |
| | | | 604/338 |
| 2009/0216206 A1* | 8/2009 | Nishtala | A61F 5/4405 |
| | | | 604/327 |
| 2016/0278969 A1* | 9/2016 | De Weert | A61F 5/448 |
| 2017/0112658 A1* | 4/2017 | Hosono | A61F 5/445 |
| 2017/0209297 A1* | 7/2017 | Lysgaard | A61F 5/4404 |
| 2018/0093146 A1* | 4/2018 | Bruce | A63B 55/408 |
| 2019/0274870 A1* | 9/2019 | Wintermute | A61F 5/4407 |

* cited by examiner

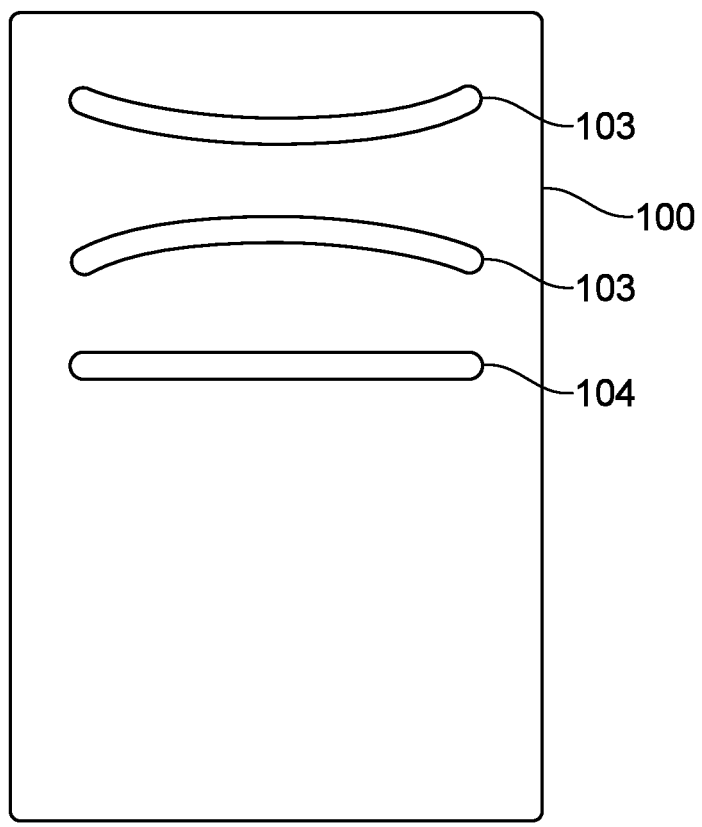
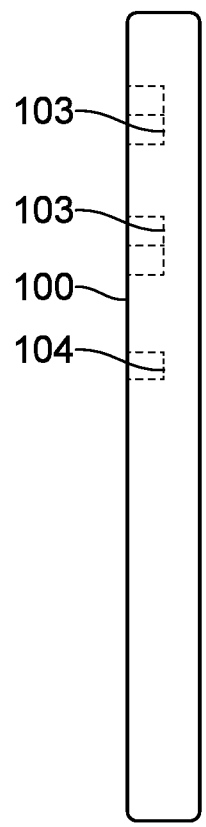
FIG. 5A     FIG. 5B

COLOSTOMY CLIP BAG HOLDER

BACKGROUND OF THE INVENTION

A. Technical Field

The present invention generally relates to a closure assistant for colostomy bag clip. More specifically, the present invention relates to a closure assistant for colostomy bag clip to help a patient in closing and opening of the colostomy bag clip.

B. Description of Related Art

Colostomy is a surgical procedure of removing a section of the colon due to a medical condition. The resulting condition from the procedure creates a situation where normal function of the bowel is no longer possible. Faeces no longer exits the body in the natural way. Sometimes, the procedure is temporary until a section of the colon is healed to resume its normal function. The colostomy is reversed in some cases. However, many cases involve a permanent colostomy especially when the damage to the colon is irreparable. The subsequent condition of the patient in case of permanent colostomy means the patient will deal with the re-routing of bowel movements to an ostomy pouching system or colostomy bag. The fitting of the colostomy bag requires a stoma or opening to be created in the abdomen to allow the waste to be collected and disposed of. The waste is collected and disposed of several times a day depending on the individual and the frequency of activity. A colostomy bag or pouch is usually replaced in every 1 to 4 days.

Closure devices for drainable pouches or colostomy bags have seen a variety of changes over the years. Previously used bulldog clamps and elastic bands have been replaced by superior integrated clips that are used to close the bags. These clips are disposed of after several uses. The closure clips allow the user to empty the contents of the bags. The use of these clips has a great advantage over the older methods in that they are more reliable. Though the clips are an outstanding improvement from the old bulldog clamps and elastic bands they still can present a problem for many people who are less able to manipulate the opening and closing of the modern clips and the proper positioning of the bag. The elderly persons who have medical issues such as arthritis face difficulty in operating the clips.

Therefore, there is a need for an assistant for colostomy bag clip to help the patient to close the bag clip. Further, there is also a need for this assistant to work for a long time and being reusable.

SUMMARY OF THE INVENTION

The present invention generally relates to a closure assistant for colostomy bag clip. More specifically, the present invention relates to a closure assistant for colostomy bag clip to help a patient in closing and opening of the colostomy bag clip.

In an embodiment, a closure assistant for colostomy clip bag is disclosed. The closure assistant is used for a clip of the colostomy bag. The closure assistant consists of a flat panel. The flat panel is a reusable flat panel. In one embodiment, the flat panel is made of a plastic material. In another embodiment, the flat panel is made of a rugged medical grade material. In one embodiment, the flat panel of the closure assistant has a plurality of slots disposed on an upper surface of the flat panel. The slots are designed to fit different types of clips of the colostomy bags. In one embodiment, the flat panel is configured to receive the colostomy bag over the upper surface to fasten the clip over the bag, thereby aiding a user to orient and fasten the clip effectively. The flat panel further comprises radiused edges to provide a comfortable grip to the user handling the closure assistant.

In one embodiment, the flat panel of the closure assistant is of, but not limited to, 7.0" to 9.0" in length. In one embodiment, the flat panel is of 3.5" to 5.5" in width. In one embodiment, the plurality of slots is of 2.5" to 4.5" in length and each slot is 0.25" in deep.

In an embodiment, the closure assistant stabilizes the process of manipulating the clips. The closure assistant aids in the location of the clip onto the colostomy bag to help eliminate mistakes with resultant malfunction. The closure assistant accommodates either curved or linear or straight type of clips. The slots of the closure assistant are of different shapes to support different kinds of clips. In one embodiment, the clip is a curve shaped clip. In some embodiments, the clip is a linear shaped clip. In one embodiment, the plurality of slots comprises at least one linear slot and two curved slots. In one embodiment, the slots comprises at least one of a rectangular shape, curve shape, arc shape, semi-arc shape, and tapered shape.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

FIG. 5A illustrates a front view of the closure assistant for colostomy bag clip, incorporating the aspects of the present invention.

FIG. 5B illustrates a side view of the closure assistant for colostomy bag clip, incorporating the aspects of the present invention.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1:
FIG. 1 illustrates a closure assistant for colostomy bag clip for helping the patient to close the bag clip, incorporating the aspects of the present invention.
Figure 3:
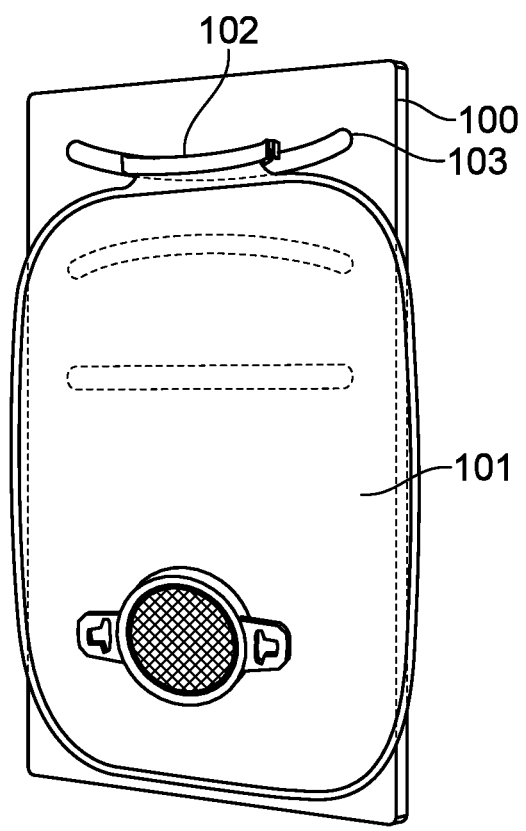
FIG. 3 illustrates a colostomy bag holder with an assistant for closing the clip of the colostomy bag, incorporating the aspects of the present invention.

The present invention relates to a closure assistant 100 for colostomy clip bag 101 as shown in FIG. 1, incorporating the aspects of the present invention. In an embodiment, the closure assistant 100 is used for a clip 102 of the colostomy bag 101. The closure assistant 100 consists of a flat panel. The flat panel is a reusable flat panel. The flat panel of the closure assistant 100 has a plurality of slots 103 and 104 in an upper surface. In another embodiment, the slots 103 and 104 are designed to fit different types of clips 102 of the colostomy bag 101. The users place the edge of the appropriately shaped clip 102 in the respective slots 103 or 104 as per the shape of the clips 102 as shown in FIG. 3. The stabilization of the clip 102 in the closure assistant 100 aids the user in closing the clip 102. The closure assistant 100 stabilizes the process of manipulating the clips 102. The closure assistant 100 aids in the location of the clip 102 onto the colostomy bag 101 to help eliminate mistakes with resultant malfunction.

Figure 2:
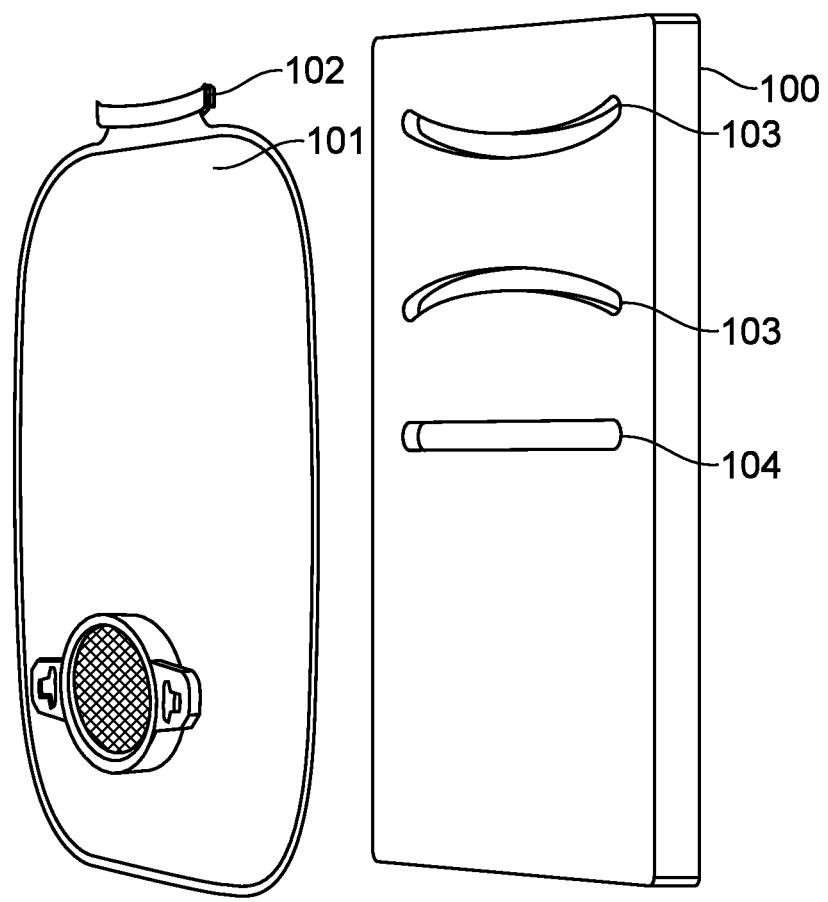
FIG. 2 illustrates a perspective view of the closure assistant for colostomy bag clip for helping the patient to close the bag clip, incorporating the aspects of the present invention.

FIG. 2 illustrates a perspective view of the closure assistant for colostomy bag clip for helping the patient to close the bag clip, incorporating the aspects of the present invention. In one embodiment, the flat panel is configured to receive the colostomy bag 101 over the upper surface to fasten the clip 102 over the bag 101, thereby aiding a user to orient and fasten the clip 102 effectively. In a preferred embodiment, the slots 103 and 104 of the closure assistant 100 are of different shapes to support different kinds of clips 102. In one embodiment, the plurality of slots (103 and 104) comprises at least one of a rectangular shape, curve shape, arc shape, semi-arc shape, and tapered shape.

In a preferred embodiment, the flat panel of the closure assistant 100 is fabricated from thick, medical grade, polyethylene plastic sheet stock. The flat panel further comprises radiused edges to provide a comfortable grip to the user handling the closure assistant 100. The polyethylene plastic used for the flat panel of the closure assistant 100 is very durable, highly resistant to household and hospital chemicals. The flat panel could be supplied in any vibrant color. In fabrication, the closure assistant 100 is cut to size on a computer-controlled water jet machining center. After cutting to shape, the closure assistant 100 is passed along to the CNC milling center where the slots are milled into the top surface. There are three slots, a linear or straight and two curved, to fit with the standard colostomy clips 102. After fabrication, the closure assistant 100 is subjected to a vibratory deburring operation to gently radius all corners and edges. After the deburring operation, closure assistant 100 is machined washed in disinfecting soap and water, rinsed, dried, and then inserted into a sanitary, vacuum sealed plastic bag.

Figure 4A:
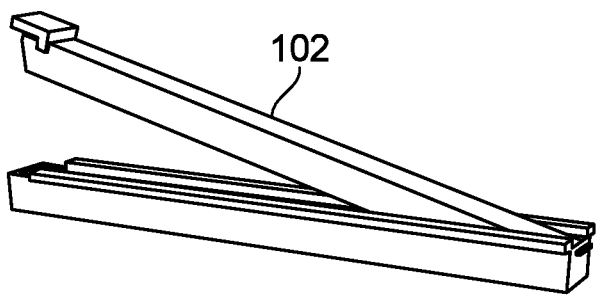
FIGS. 4A-4B illustrates different types of clips to be used for the colostomy bags, incorporating the aspects of the present invention.
Figure 4B:
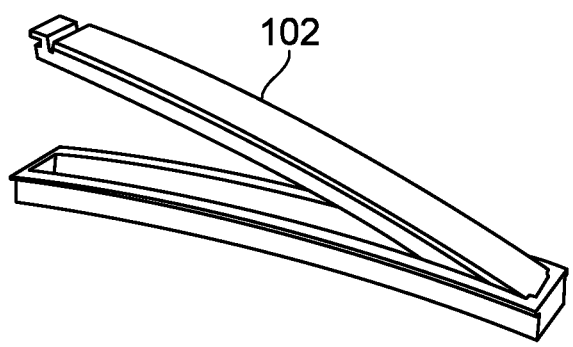

The closure assistant 100 consists of different types of slots 103 and 104 to fit different types of clips 102 of the colostomy bag 101. The closure assistant 100 accommodates either curved or linear type of clips 102. FIGS. 4A-4B, the clip 102 is a linear shaped clip. In another embodiment, the clip 102 is a curve shaped clip. The slots 103 and 104 of the closure assistant 100 configured to accommodates either the curved or linear type of clips 102.

FIG. 5A illustrates a front view of the closure assistant 100 for the clip 102 of the colostomy bag 101, incorporating the aspects of the present invention. In an embodiment, a medical grade plastic sheet is cut to shape of vertical edges and the rounded corners, using a water jet machining center. The closure assistant 100 is slotted using computer numerically controlled milling center and a diameter milling bit. The closure assistant 100 holds either curved or linear clips 102 securely and assists the user while they close the clip on the colostomy bag. In another embodiment, the slot 103 on the closure assistant 100 is meant for a curved clip 102 (shown in FIG. 4B) and the slot 104 on the closure assistant 100 is meant for a linear clip 102 (shown in FIG. 4A).

FIG. 5B illustrates a side view of the closure assistant 100 for colostomy bag clip 102, incorporating the aspects of the present invention. In one embodiment, the flat panel of the closure assistant 100 is of, but not limited to, 7.0" to 9.0" in length. In one embodiment, the flat panel is of, but not limited to, 3.5" to 5.5" in width. In one embodiment, the plurality of slots (102 and 103) is of, but not limited to, 2.5" to 4.5" in length and each slot is 0.25" in deep.

In a preferred embodiment, the closure assistant 100 helps the patients, suffering from medical issues requiring an ostomy pouching system or colostomy bag 101 and the related problems of using colostomy bag 101. The closure assistant 100 comes with simple sturdy construction and easy to operate. The closure assistant 100 is made up of medical grade quality materials. The closure assistant 100 helps in locating clips 102 for closing, by applying straight forward pressure rather than a pinching or squeezing motion. The slots 103 and 104 on the closure assistant 100 are located as a measuring standard to give the proper distance to fold the colostomy bag 101 before closure with the clip 102.

Preferred embodiments of this invention are described herein, including the best mode known to the inventors for carrying out the invention. It should be understood that the illustrated embodiments are exemplary only and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A closure assistant for a colostomy bag, comprises:
   a single flat panel; and
   a plurality of slots disposed on an upper surface of the single flat panel,
   wherein the colostomy bag is configured to attach to the single flat panel;
   wherein each slot is configured to detachably receive a clip, and wherein the single flat panel is configured to receive the colostomy bag over the upper surface to fasten the clip over the bag, thereby aiding a user to orient and fasten the clip effectively;
   wherein the slots include a rectangular shape slot; wherein the slots include a curve shape slot; wherein the slots include an arc shape slot; wherein the slots include a semi-arc shape slot; wherein the slots include a tapered shape slot; wherein the rectangular shape slot is of a different size than the curved shape slot; wherein the arc shaped slot is of a different size than the curved-shaped slot; wherein the semi-arc shaped slot is of a different size than the arc-shaped slot; wherein the arc shaped slot is of a different size than the semi-arc-shaped slot; and wherein the semi-arc shaped slot is of a different size than the tapered shape slot.

2. The closure assistant of claim 1, wherein each slot is of different size to support different kinds of clips.

3. The closure assistant of claim 1, wherein the plurality of slots comprises at least one linear slot.

4. The closure assistant of claim 1, wherein the plurality of slots comprises at least two curved slots.

5. The closure assistant of claim 1, wherein the single flat panel is made of a plastic material.

6. The closure assistant of claim 1, wherein the plurality of slots comprises at least one of a rectangular shape, curve shape, arc shape, semi-arc shape, and tapered shape.

7. The closure assistant of claim 1, wherein the single flat panel is made of a rugged medical grade material.

8. The closure assistant of claim 1, wherein the single flat panel comprises raised edges to provide a comfortable grip to the user handling the closure assistant.

9. The closure assistant of claim 1, wherein the single flat panel is a reusable flat panel.

10. The closure assistant of claim 1, wherein the clip is a curve shaped clip.

11. The closure assistant of claim 1, wherein the clip is a linear shaped clip.

12. The closure assistant of claim 1, wherein the single flat panel is of 7.0" to 9.0" in length.

13. The closure assistant of claim 1, wherein the single flat panel is of 3.5" to 5.5" in width.

14. The closure assistant of claim 1, wherein the plurality of slots is of 2.5" to 4.5" in length.

15. The closure assistant of claim 1, wherein each slot is 0.25" in deep.

* * * * *